US008652139B2

(12) United States Patent
Sterrett et al.

(10) Patent No.: US 8,652,139 B2
(45) Date of Patent: Feb. 18, 2014

(54) FLIP RETROGRADE CUTTING INSTRUMENT

(75) Inventors: Jerry Sterrett, Naples, FL (US); David Koogle, Naples, FL (US); Ronald C. Iannarone, Aiken, SC (US); Ricardo Albertorio, Naples, FL (US)

(73) Assignee: Arthrex, Inc., Naples, FL (US)

( * ) Notice: Subject to any disclaimer, the term of this patent is extended or adjusted under 35 U.S.C. 154(b) by 991 days.

(21) Appl. No.: 12/114,599

(22) Filed: May 2, 2008

(65) Prior Publication Data

US 2009/0275950 A1    Nov. 5, 2009

Related U.S. Application Data

(60) Provisional application No. 60/915,607, filed on May 2, 2007.

(51) Int. Cl.
*A61B 17/56* (2006.01)
(52) U.S. Cl.
USPC ......................................... 606/80; 606/86 R
(58) Field of Classification Search
USPC ....... 606/84, 102, 96, 79–80, 86 R, 167, 170, 606/180
See application file for complete search history.

(56) References Cited

U.S. PATENT DOCUMENTS

| | | | |
|---|---|---|---|
| 4,341,206 A * | 7/1982 | Perrett et al. | 606/80 |
| 5,429,504 A | 7/1995 | Peltier et al. | |
| 5,928,239 A | 7/1999 | Mirza | |
| 5,941,706 A | 8/1999 | Ura | |
| 6,015,411 A * | 1/2000 | Ohkoshi et al. | 606/80 |
| 6,884,246 B1 | 4/2005 | Sonnabend et al. | |
| 7,172,599 B2 * | 2/2007 | Steffensmeier et al. | 606/102 |
| 7,238,189 B2 * | 7/2007 | Schmieding et al. | 606/80 |
| 7,914,545 B2 * | 3/2011 | Ek | 606/180 |
| 2001/0034526 A1 | 10/2001 | Kuslich et al. | |
| 2004/0106940 A1* | 6/2004 | Shaolian et al. | 606/170 |
| 2004/0199166 A1* | 10/2004 | Schmieding et al. | 606/79 |
| 2005/0261684 A1 | 11/2005 | Shaolian et al. | |
| 2006/0195112 A1* | 8/2006 | Ek | 606/86 |
| 2007/0233138 A1 | 10/2007 | Figueroa et al. | |

FOREIGN PATENT DOCUMENTS

| | | |
|---|---|---|
| EP | 0 241 240 A2 | 10/1987 |
| EP | 1 785 103 A1 | 5/2007 |
| FR | 2 613 212 A1 | 10/1988 |

* cited by examiner

*Primary Examiner* — Nicholas Woodall
*Assistant Examiner* — Larry E Waggle, Jr.
(74) *Attorney, Agent, or Firm* — Dickstein Shapiro LLP

(57) ABSTRACT

A flip retrograde cutting instrument and method of retrograde drilling using such an instrument. A method of forming a socket includes providing a flip retrograde cutter, inserting the cutter into a joint with a blade of the cutter in a straight position, pivoting the blade to a non-straight flip position, locking the blade in the flip position, and retrograde drilling a socket using the blade in the flip position.

4 Claims, 5 Drawing Sheets

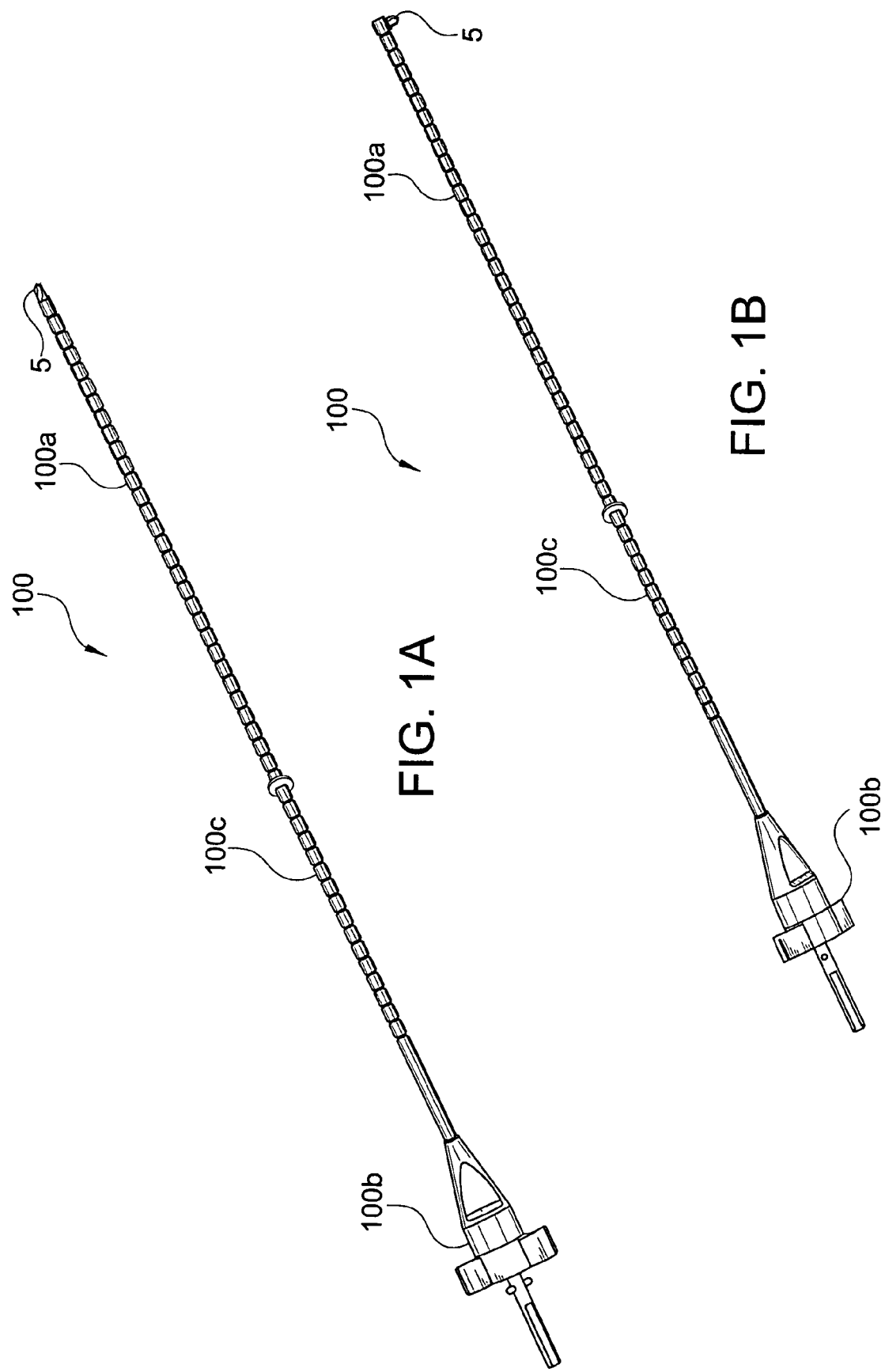

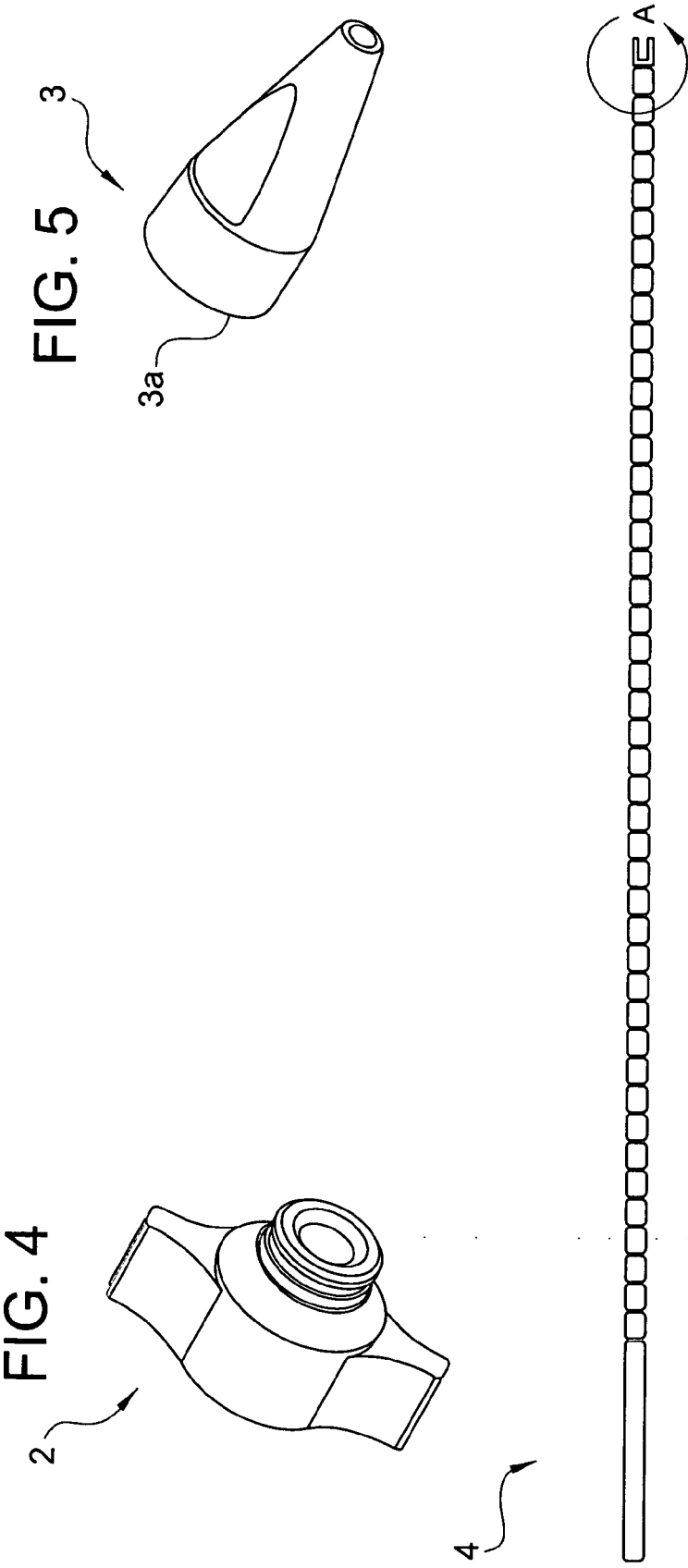

FLIP RETROGRADE CUTTING INSTRUMENT

CROSS-REFERENCE TO RELATED APPLICATIONS

This application claims priority to U.S. Provisional Application No. 60/915,607, filed on May 2, 2007, the entire contents of which are hereby incorporated by reference.

BACKGROUND OF THE INVENTION

1. Field of the Invention

The present invention relates to arthroscopic surgical methods and instruments and, more specifically, to a flip retrograde cutting instrument and methods of retrograde repairs and reconstructions.

2. Description of the Related Art

During arthroscopic surgery, a small incision is made in the skin covering the arthroscopic site or joint, and a cannula is inserted in the incision to provide a pathway for surgical instruments to be placed in the joint and manipulated through arthroscopic visualization. Surgical instruments inserted through cannulas must be long and thin—this presents limitations on instruments for cutting tissue, as the diameter of the cannula ordinarily limits the width of the cutting implement.

Retrograde drilling of sockets and tunnels for ACL reconstruction is known and described, for example, in U.S. Patent Application Publication No. 2007/0233138, entitled "Method and Apparatus for ACL Reconstruction using Retrograde Cutter", the disclosure of which is incorporated by reference herein. In such a method, sockets in bone created by retrograde cutting. A rotary cutter, mounted onto an insertion post of a guide, is inserted through an anteromedial portal into the knee joint. A drill pin is drilled through the tibia and advanced until it contacts and engages a cannulation in the rotary cutter on the guide. Further rotation of the drill pin disengages the rotary cutter from the guide. The retrograde drill pin is then retracted and simultaneously rotated for retrograde cutting of a socket or tunnel of desired depth in the tibia. A similar method can be used for drilling a femoral socket or tunnel. A need exists for a surgical cutting instrument that can be used arthroscopically for retrograde drilling of tunnels or sockets in bone without requiring a rotary cutter and drill pin. As with all arthroscopic instruments, the surgical cutting instrument must be configured for insertion through a narrow cannula, but able to cut a relatively wide tunnel or socket.

A need also exists for a surgical cutter that is stable during knee arthroscopy and that provides drilling of femoral and tibial sockets or tunnels independently of one another and minimizes incisions of distal cortices and reduces intraarticular bone fragmentation of tunnel rims.

SUMMARY OF THE INVENTION

The present invention provides a flip retrograde cutter having a blade, preferably a flip blade, that is configured to articulate between at least a first "straight" position, for example, substantially parallel to a longitudinal axis of the flip retrograde cutter, and at least a second "flip" position, for example, a non-parallel position relative to the longitudinal axis of the flip retrograde cutter.

The present invention provides a flip retrograde cutter that creates a recipient site socket from the inside out, i.e., using a retrograde technique, with minimal incisions of distal cortices and reduced intraarticular bone fragmentation of tunnel rims.

The flip retrograde cutter of the present invention may be employed in a retrograde manner, to form a recipient socket (to accommodate an osteochondral transplant, or to allow retrograde fixation of a graft within two sockets, for example). Formation of the recipient socket begins by inserting the flip retrograde cutter in the "straight" configuration into the joint space, preferably from the outside in, through a small diameter tunnel. A locking tube of the instrument is then retracted so that the blade can be articulated into the "flip" configuration, i.e., into a position other than the "straight" position and preferably at about 90 degrees to the longitudinal axis of the instrument. The device is locked in the "flip" position by tightening the locking tube. A socket is created by conducting a drilling operation, i.e., by rotating the instrument, while the device is pulled outwardly.

Other features and advantages of the invention will become apparent from the following description of the invention, which refers to the accompanying drawings.

BRIEF DESCRIPTION OF THE DRAWINGS

FIGS. 1A-1B illustrate perspective views of a flip retrograde cutter of the present invention showing the blade in straight and flip positions.

FIG. 4 illustrates a perspective view of a nut of the flip retrograde cutter of the present invention.

FIG. 5 illustrates a perspective view of a hub of the flip retrograde cutter of the present invention.

FIGS. 6A-6B illustrate various views of a locking tube of the flip retrograde cutter of the present invention.

DETAILED DESCRIPTION OF THE PREFERRED EMBODIMENT

Figure 2A:
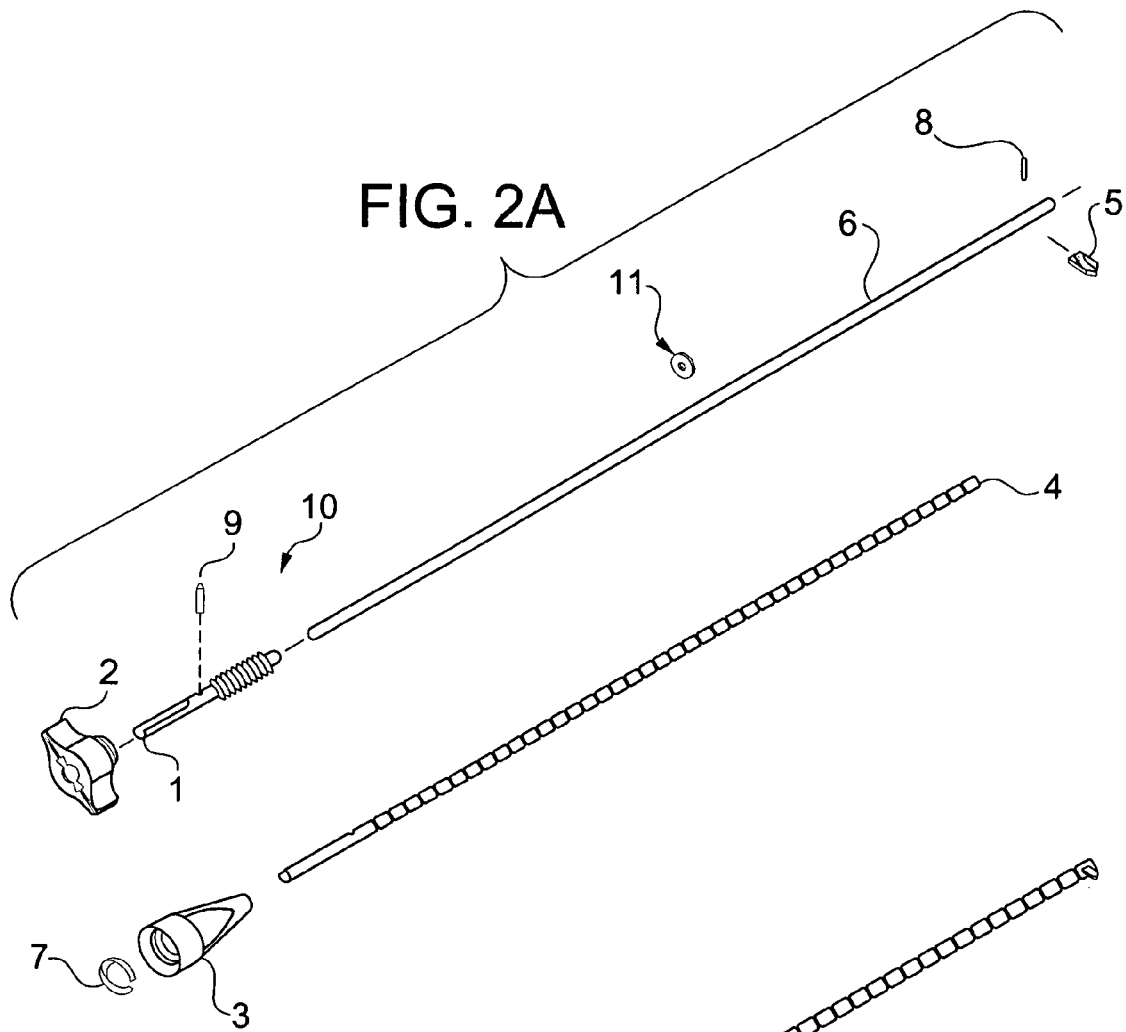
FIGS. 2A-2B illustrate an exploded view and a perspective view of the flip retrograde cutter of the present invention.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Referring now to the drawings, where like elements are designated by like reference numerals, FIGS. 1-8 illustrate various components of a flip retrograde cutter 100 of the present invention. The flip retrograde cutter 100 creates a recipient site socket from the inside out, i.e., using a retrograde technique, with minimal incisions of distal cortices and reduced intraarticular bone fragmentation of tunnel rims.

Figure 2B:
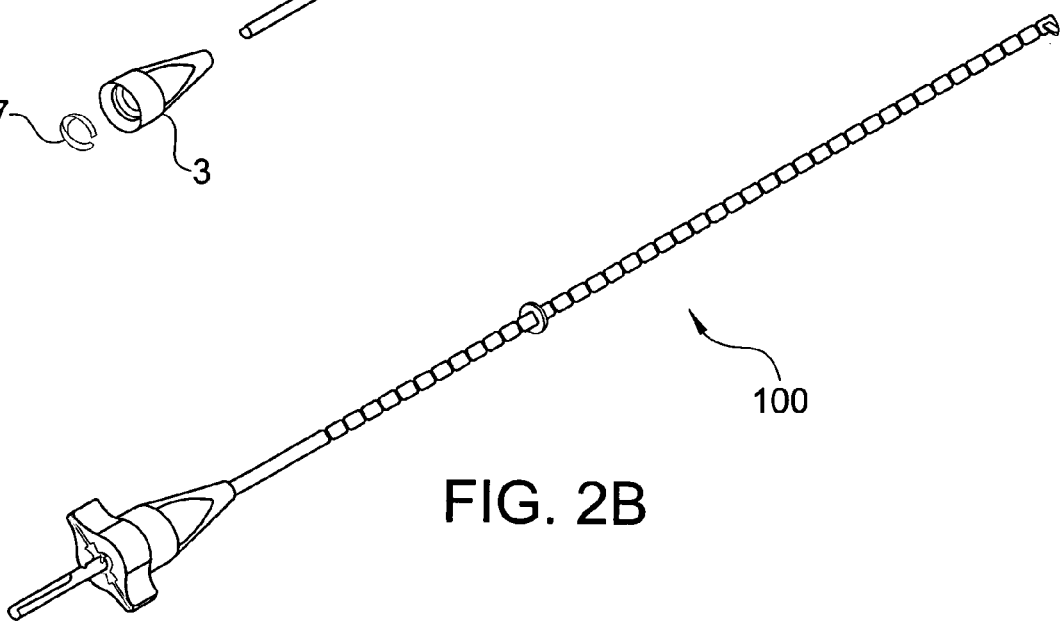
Figure 3A:
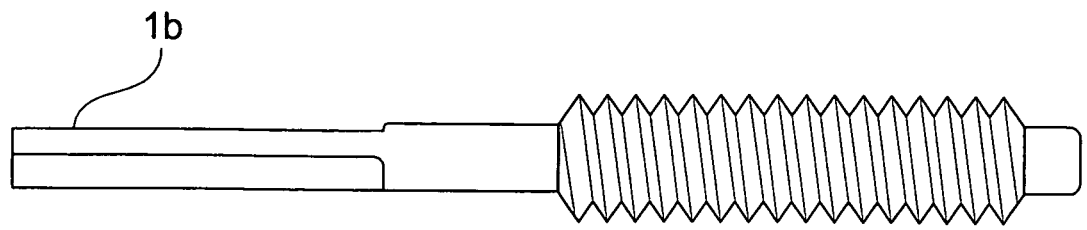
FIGS. 3A-3C illustrate various views of a driver end of the flip retrograde cutter of the present invention.
Figure 3B:
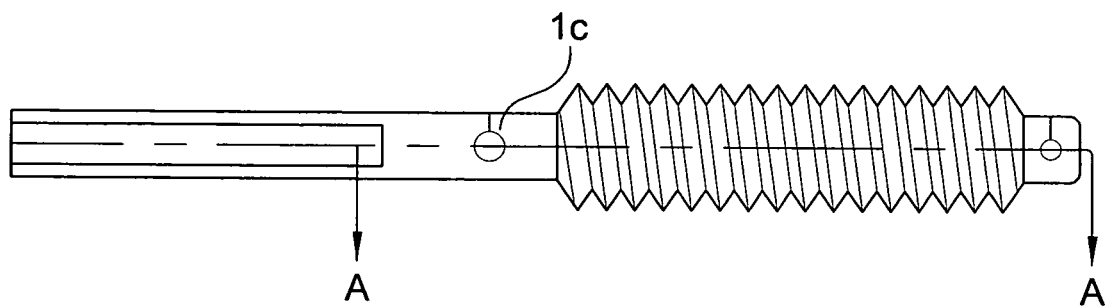
Figure 3C:
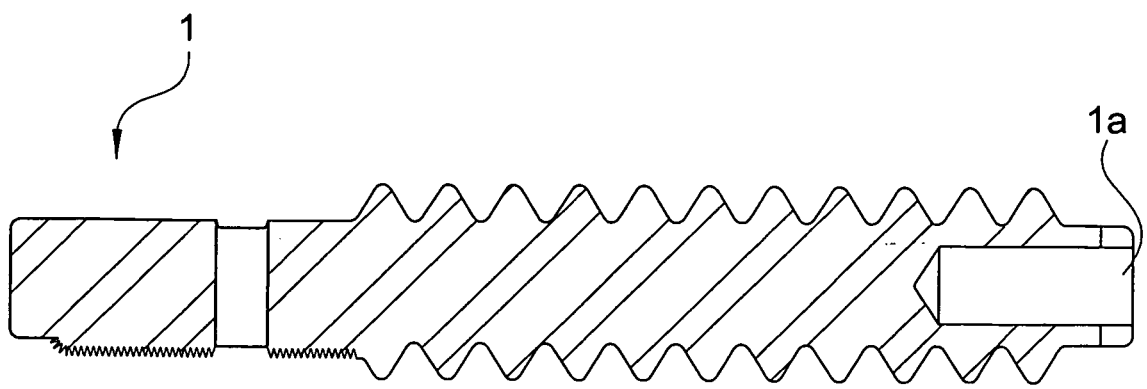
Figure 8B:
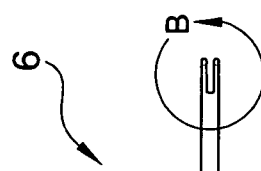
FIGS. 8A-8B illustrate various views of a shaft of the flip retrograde cutter of the present invention.

The flip retrograde cutter 100 includes a cannulated elongated body 100c having a distal end 100a and a proximal end 100b, as shown in FIG. 1. The body 100c of the flip retrograde cutter 100 includes a shaft 6 and a locking tube 4, with a blade 5 at the distal end 100a of the instrument, as shown in FIGS. 2A-2B. The following is a list of parts of the flip retrograde cutter 100: driver end 1, nut 2, hub 3, locking tube 4, blade/cutter tip 5, shaft 6, retainer ring 7, cross pin 8, slotted spring pin 9, pin 10 and O-Ring 11. Details of the various parts of the flip retrograde cutter 100 are illustrated in FIGS. 2-8 and listed below in Table 1.

TABLE 1

| Apparatus of the present invention | |
|---|---|
| Flip Retrograde Cutter | |
| Overall dimensions: | 13.58 inches (length) × 3.5 mm (shaft diameter) |
| | 10.75 inches (length from hub to blade) |
| Cutting diameter: | 6-13 mm. Blade rotates freely and locks in straight and 90 degree positions. |
| Driver End | |
| Overall dimensions: | 2.1 inches (length) × 0.156 inches (diameter of unthreaded portion) |
| Thread size: | ¼-20 UNC-2A (¼ inches diameter with 20 threads/inch). The threads start 0.1 inch from one end. |
| Unthreaded portion: | 1.13 inches (length) with a through hole of 0.063 diameter at 0.96 inch from one end. |
| Material: | 18-8 Stainless Steel; clean and electropolish finish |
| Nut | |
| Overall dimensions: | 0.365 inches (inner diameter of through hole) × 0.585 inches (width). |
| Thread Size: | ¼-20 UNC-2B |
| Material: | Polylac PA-747 Acrylonitrile butadiene styrene (ABS) |
| Color: | Blue |
| Hub | |
| First Portion: | 0.625 inches (outer diameter) × 0.383 inches (height) × 2° slope between the diameters at both ends of the first portion. |
| Second Portion: | 0.979 inches (height) × 24° slope between the diameters at both ends of the first portion. |
| Material: | Polylac PA-747 Acrylonitrile butadiene styrene (ABS) |
| Color: | Blue |
| Locking Tube | |
| Overall dimensions: | 0.134 inches (diameter) × 11.05 inches (length) |
| | Tube has a slot on one end having a width of 0.04 inches and a length of 0.175 inches from the end. |
| | Laser etch lines around circumference of the tube. |
| Material: | 17-7 Stainless Steel Condition A; clean and electropolish finish. |
| Blade | |
| Overall dimensions: | 118° (tip angle) × 0.138 inches (cutting radius) |
| Effective cutting diameter: | 6-13 mm |
| Material: | 17-4 PH Stainless Steel; clean and electropolish finish |
| Shaft | |
| Overall dimensions: | 0.102 inches (diameter) × 11.625 inches (length). |
| | One end of the shaft has a through hole 0.15 inches from the end and having a diameter of 0.04 inches. Another end has a slot with a slot width of 0.04 inches and a length of 0.175 inches from the end. The slotted end also has a through hole having a diameter of 0.04 inches. |
| Material: | 17-4 PH Stainless Steel; clean and electropolish finish. |
| Retainer Ring | |
| Overall dimensions: | 0.475 inches (outer diameter) × 0.375 inches (inner diameter) × 0.125 inches (slot gap) × 0.032 inches (thickness). |
| Material: | Polylac PA-747 Acrylonitrile Butadiene Styrene (ABS) |
| Color: | Blue |
| Cross Pin | |
| Overall dimensions: | 0.0396 inches (diameter) × 0.1 inches (length) |
| Material: | 18-8 Stainless Steel |
| Slotted Spring Pin | |
| Overall dimensions: | 1/16 inches (diameter) × 3/8 inches (length) |
| Material: | 18-8 Stainless Steel |
| Pin | |
| Overall dimensions: | 1 mm × 4 mm |
| Material: | 18-8 Stainless Steel |
| O-Ring | |
| Overall dimensions: | 0.25 inches (outer diameter) × 0.125 inches (inner diameter) |
| Basic shape: | Round in plan shape |
| Material: | Viton |
| Color: | Black |

The flip retrograde cutter 100 is preferably assembled by first pressing the locking tube 4 into the hub 3 until the locking tube 4 bottoms out. The retainer ring 7 is then inserted into a groove 3a of the hub 3 to form a first sub-assembly.

Next, the shaft 6 is slide into end 1a of the driver end 1 and securely engaged using the pin 10. The first sub-assembly, described above, is slide over the assembled shaft 6 and driver end 1. Next, the blade 5 is slide into slot 6a of the shaft 6 and securely engaged using the cross pin 8, subsequently welding in place the cross pin 8 at both its ends. The nut 2 is then screwed onto end 1b of the driver end 1. Next, the hub 3 is pulled back while advancing the nut 2 until the retainer ring 7 engages and the slotted spring pin 9 is inserted into a through hole 1c in the driver end 1 to secure the driver end 1 against the nut 2. The O-Ring 11 is slide over the locking tube 4, having laser etches 4 a on its circumference, until the O-Ring 11 is about 3-5 inches from the hub 3. The O-Ring 11 may be used to measure depth during retrograde drilling.

Figure 7:
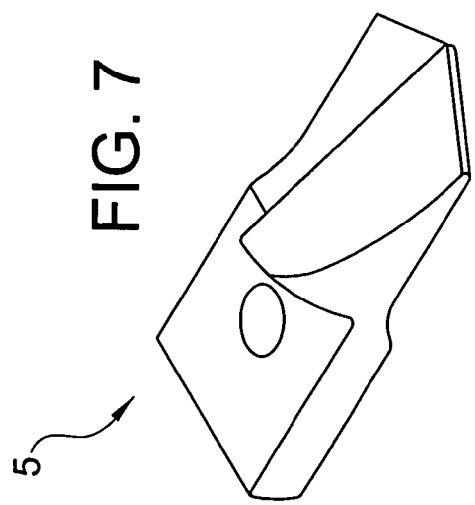
FIG. 7 illustrates a perspective view of a blade/cutter tip of the flip retrograde cutter of the present invention.
Figure 8A:
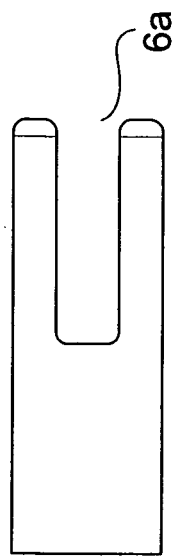

Details of the blade 5 of the flip retrograde cutter 100 are illustrated in FIG. 7; however, the invention contemplates other shapes and geometries for the blade 5. The blade 5 is configured to engage the shaft 6 and to articulate between at least first and second positions. In an exemplary embodiment, blade 5 engages shaft 6 in a first or "straight" position (FIG. 1A), for example, about parallel to the longitudinal axis of the cutting instrument 100. The blade 5 also engages shaft 6 in a second or "flip" position (FIG. 1B), for example, a non-parallel position relative to the longitudinal axis of the cutting instrument 100, preferably about 90 degrees relative to the longitudinal axis. The present invention, however, contemplates embodiments wherein the blade 5 forms any angle with the shaft 6, for example, an angle between about 10 to about 170 degrees relative to the longitudinal axis of the cutting instrument 100.

In use, once the flip retrograde cutter 100 is inserted into a joint, for example, a knee joint, the surgeon rotates the nut 2 to allow the locking tube 4 of the flip retrograde cutter 100 to retract. The blade 5 is then articulated, for example by manipulating it with another instrument, so that it is pivoted into the "flip" position, i.e., into a position other than the "straight" position, preferably 90 degrees to the longitudinal axis of the instrument. The surgeon may modify the angle of the blade, as desired and in accordance with the characteristics of the surgical site. Once the blade 5 is articulated in the desired "flip" position, the blade 5 is preferably locked by tightening the locking tube 4. A drilling operation, for example, a retrodrilling step, may be subsequently carried, as known in the art.

According to an exemplary embodiment, the flip retrograde cutter 100 of the present invention may be employed in a retrograde manner to form a recipient socket (at the location of an osteochondral lesion developed on the head of the tibia, for example, or to accommodate retrograde fixation of a graft within two sockets). Formation of the recipient socket begins by inserting the flip retrograde cutter 100 in the "straight" configuration into the joint space, preferably from the outside in, through a small diameter tunnel (for example, of less than about 4 mm). The locking tube 4 of the instrument is then retracted and the blade 5 is articulated into the "flip" configuration (i.e., into a position other than the "straight" position). The "flip" position is preferably locked by tightening the locking tube 4 to allow a drilling operation to take place.

The present invention may be used to form various sockets or tunnels for graft fixation or to create sockets in a retrograde manner for replacement osteochondral cores or implants, obviating the need for inserting harvesters into the joint. For example, the flip retrograde cutting instrument 100 of the present invention may be employed for the formation of sockets during an "All-Inside ACL RetroConstruction" ligament repair, by drilling at least a femoral and tibial tunnel or socket using a retrodrill technique employing the flip retrograde cutting instrument 100 of FIGS. 1-2. A graft (soft tissue graft or BTB graft) may be provided in the vicinity of the sockets and the graft secured within the femoral and tibial tunnels (sockets).

According to yet another embodiment, an exemplary method of ACL RetroConstruction of the present invention includes drilling a femoral socket, and drilling a tibial tunnel or socket using a retrodrill technique employing the flip retrograde cutting instrument 100 of FIGS. 1-2. Next, a graft (soft tissue graft or BTB graft) is provided in the vicinity of the sockets and the graft is secured to a continuous loop/button construct having a button with an oblong configuration and provided with an inside eyelet that allows the passage of the continuous loop, preferably a suture loop. The graft is passed with the button through the femoral tunnel and the button is secured to the femoral cortex once the button exits the femoral socket. Finally, the graft is secured in the tibial tunnel or socket.

Although the above-detailed methods of socket formation using the flip retrograde cutter 100 of the present invention have been described with reference to a specific ACL reconstruction, i.e., a specific "all-inside ACL RetroConstruction" for ligament repair, the invention is not limited to this exemplary embodiment, and contemplates any repairs and reconstructions that employ a cutting instrument such as flip retrograde cutter 100 of the present invention.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of ligament reconstruction including forming a bone tunnel or socket in a first bone normally articulating in a predetermined manner with a second bone at an articular joint, comprising:

inserting a flip retrograde cutter through a pre-formed tunnel of a diameter of less than about 4 mm in the first bone and into an articular joint space of the articular joint in a straight position, the flip retrograde cutter comprising a cannulated elongated body having a distal end, a proximal end and a longitudinal axis, the body further comprising a shaft having a blade disposed at its distal end, the blade being securely engaged to the shaft and capable of movement from the straight position to a flip position and vice versa, the blade having a cutting diameter of about 6 mm to about 13 mm, the body further comprising a locking tube housing the shaft;

subsequently, while the blade is in the straight position, retracting the locking tube to allow the blade to articulate and to flip, within the joint space, from the straight position wherein the blade is aligned with the longitudinal axis of the shaft to the flip position which is not aligned with the longitudinal axis of the shaft and wherein the blade faces the proximal end of the body for retrograde drilling of a bone tunnel or socket;

locking the blade in the flip position by tightening the locking tube;

pulling the retrograde cutter proximally so that the blade in the flip position cuts in a retrograde manner in the first bone, from the articular joint space towards an outer surface of the first bone, and drills the bone tunnel or socket using the flip retrograde cutter with the blade in the flip position; and inserting a graft in the bone tunnel or socket; and securing the graft in the bone tunnel or socket.

2. The method of claim 1, wherein the blade is articulated to an angle of about 10° to about 170° to the longitudinal axis of the shaft of the flip retrograde cutter when the blade is in the flip position.

3. The method of claim 1, wherein the blade is articulated to an angle of about 90° to the longitudinal, axis of the shaft of the flip retrograde cutter when the blade is in the flip position.

4. The method of claim 1, wherein the locking tube is provided with laser etch markings on its circumference, the etch markings being provided at regular intervals to facilitate depth measurement.

* * * * *